(12) United States Patent
Pintado

(10) Patent No.: US 10,307,307 B2
(45) Date of Patent: Jun. 4, 2019

(54) SANITARY PAD WITH A CREVICE MOUND AND A METHOD OF USING SAME

(71) Applicant: Zara C. Pintado, Fishkill, NY (US)

(72) Inventor: Zara C. Pintado, Fishkill, NY (US)

( * ) Notice: Subject to any disclaimer, the term of this patent is extended or adjusted under 35 U.S.C. 154(b) by 441 days.

(21) Appl. No.: 15/085,962

(22) Filed: Mar. 30, 2016

(65) Prior Publication Data
US 2017/0281419 A1 Oct. 5, 2017

(51) Int. Cl.
| | |
|---|---|
| A61F 13/472 | (2006.01) |
| A61F 13/56 | (2006.01) |
| A61F 13/15 | (2006.01) |

(52) U.S. Cl.
CPC .... *A61F 13/47227* (2013.01); *A61F 13/5616* (2013.01); *A61F 2013/1513* (2013.01)

(58) Field of Classification Search
CPC .............. A61F 13/472; A61F 13/47209; A61F 13/47218; A61F 13/47227; A61F 2013/1513; A61F 2013/4729
See application file for complete search history.

(56) References Cited

U.S. PATENT DOCUMENTS

| | | | | |
|---|---|---|---|---|
| 6,348,047 B1* | 2/2002 | Harper | ............. | A61F 13/47227 604/385.01 |
| 6,652,503 B1* | 11/2003 | Bradley | ............ | A61F 13/47272 604/385.01 |
| 6,965,058 B1* | 11/2005 | Raidel | ............... | A61F 13/47218 604/367 |
| 7,530,973 B2* | 5/2009 | Tanio | .................. | A61F 13/4702 604/380 |
| 8,870,842 B2* | 10/2014 | Hill | ....................... | A61F 13/475 604/385.17 |
| 2005/0027278 A1* | 2/2005 | Mizutani | ........... | A61F 13/47209 604/387 |

* cited by examiner

*Primary Examiner* — Catharine L Anderson
(74) *Attorney, Agent, or Firm* — Aziz M. Ahsan; Ahsan & Associates, PLLC

(57) ABSTRACT

The present invention relates generally to a sanitary pad with a crevice mound and a method of using same. More particularly, the invention encompasses a sanitary pad having at least one crevice mound or male portion or raised padded projection, and where the at least one crevice mound physically and partially penetrates an area near and around a human orifice, such as, anal crevice area, vaginal crevice area, to intercept, collect, and retain any bodily fluid that maybe being discharged from the human orifice around the vaginal and/or anal area. The invention also provides a method of using the inventive sanitary pad with at least one crevice mound, where the crevice mound is placed near or adjacent a human orifice, such as, anus, vagina, to at least capture at least a portion of a human bodily fluid coming out of the human orifice around the anal and/or vaginal area.

20 Claims, 1 Drawing Sheet

SANITARY PAD WITH A CREVICE MOUND AND A METHOD OF USING SAME

FIELD OF THE INVENTION

The present invention relates generally to a sanitary pad with a crevice mound and a method of using same. More particularly, the invention encompasses a sanitary pad having at least one crevice mound or male portion or raised padded projection, and where the at least one crevice mound physically and partially penetrates an area near and around a human orifice, such as, anal crevice area, vaginal crevice area, to intercept, collect, and retain any bodily fluid that maybe being discharged from the human orifice around the vaginal and/or anal area. The invention also provides a method of using the inventive sanitary pad with at least one crevice mound, where the crevice mound is placed near or adjacent a human orifice, such as, anus, vagina, to at least capture at least a portion of a human bodily fluid coming out of the human orifice around the anal and/or vaginal area.

BACKGROUND INFORMATION

Sanitary pads have been used in the feminine hygiene and medial industry for a variety of reasons, and they come in many shapes, sizes, and other physical features and attributes.

The most common use of sanitary pads is by women who are going through their normal menstruation cycle, which typically recurs for non-pregnant breeding-age women at approximately monthly intervals, which is also commonly referred to as her "period.". It involves the menstrual flow or menses, which is a discharge of blood, secretions, and tissue debris from the uterus via the vagina. The monthly menstrual bleeding typically requires a woman to use a pad or similar such hygiene material to capture the menses. However, these pads or hygiene material have a flat surface when laid on a flat plane or surface, and thus these pads or hygiene material also form a flat surface when placed in situ near the outer surface of the vagina.

This invention improves on the deficiencies of the prior art and provides an inventive sanitary pad with a crevice mound and a method of using same.

PURPOSES AND SUMMARY OF THE INVENTION

The invention is a novel sanitary pad with a crevice mound and a method of using same.

Therefore, one purpose of this invention is to provide a sanitary pad with a crevice mound and a method of using same.

Another purpose of this invention is to provide a sanitary pad having at least one crevice mound or male portion, and where the at least one crevice mound or male portion physically and partially penetrates an area near or adjacent a human orifice, such as, anus, vagina, to intercept, collect, and retain any bodily fluid that may be coming out of the human orifice.

Yet another purpose of this invention is to provide a sanitary pad having at least one crevice mound, and where the at least one crevice mound physically and partially penetrates an area near an orifice to intercept, collect, and retain any bodily fluid that may be coming out of the human orifice, and wherein the at least one crevice mound comprises of at least one fluid absorbing material.

Therefore, in one aspect this invention comprises a feminine hygiene device, comprising:
(a) at least one first fluid absorbing layer having a top surface and a bottom surface;
(b) at least one second fluid absorbing layer, wherein said second fluid absorbing layer is in physical contact with said top surface of said at least one first fluid absorbing layer, and wherein said at least one second fluid absorbing layer comprises of at least one male portion; and
(c) at least one layer of at least one fluid impervious material secured to at least a portion of said bottom surface of said at least one first fluid absorbing layer.

In another aspect this invention comprises a hygiene device, comprising:
(a) at least one first fluid absorbing layer having a top surface and a bottom surface;
(b) at least one second fluid absorbing layer, wherein said second fluid absorbing layer is in physical contact with said top surface of said at least one first fluid absorbing layer, and wherein said at least one second fluid absorbing layer comprises of at least one male portion; and
(c) at least one layer of at least one fluid impervious material secured to at least a portion of said bottom surface of said at least one first fluid absorbing layer.

In yet another aspect this invention comprises a feminine hygiene device in the nature of a feminine pad, comprising:
(a) at least one first fluid absorbing layer having a top surface and a bottom surface;
(b) at least one second fluid absorbing layer, wherein said second fluid absorbing layer is in physical contact with said top surface of said at least one first fluid absorbing layer, and wherein said at least one second fluid absorbing layer comprises of at least one male portion;
(c) at least one layer of at least one fluid impervious material secured to at least a portion of said bottom surface of said at least one first fluid absorbing layer; and
(d) wherein said at least one male portion is disposed to be placed inside a user's vaginal area.

BRIEF DESCRIPTION OF THE DRAWINGS

The invention may best be further understood by reference to the ensuing detailed description in conjunction with the drawings in which.

DETAILED DESCRIPTION

Figure 1:
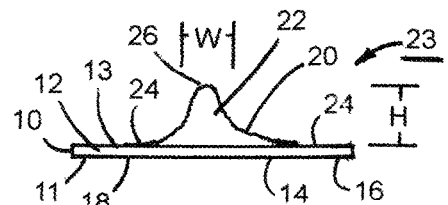
FIG. 1, illustrates a side view of an inventive sanitary pad with a crevice mound, according to a first embodiment of this invention.

The inventive sanitary pad with a crevice mound and a method of using same will now be discussed with reference to FIGS. 1 through 9. Although the scope of the present invention is much broader than any particular embodiment, a detailed description of the preferred embodiment follows together with drawings. These drawings are for illustration purposes only and are not drawn to scale. Like numbers represent like features and components in the drawings.

Furthermore, this inventive sanitary pad having at least one crevice mound, and where the at least one crevice mound physically and partially penetrates an area near an orifice to intercept and collect any fluid that may be coming out of the orifice in one aspect comprises of at least one vertical upside down "V" going across at least a portion of the sanitary pad. The material on the sanitary pad has to be able to be extra absorbent and be capable of intercepting and retaining bodily fluids.

FIG. 1, illustrates a side view of an inventive sanitary pad with a crevice mound or hygiene device 23, according to a first embodiment of this invention. The inventive sanitary pad 23, has a base or pad 10, having at least one first or base fluid absorbing material 12, contained therein. For some applications the base or pad 10, and the at least one base fluid absorbing material 12, could be one and the same thing or interchangeable. The base or pad 10, has a first or lower or bottom side or surface 11, and a second or upper or top side or surface 13. The bottom side 11, of the base or pad, preferably has at least one layer of at least one adhesive material 14, which material 14, may be temporarily protected by at least one protective layer 16. The upper surface 13, of the base 10, has secured thereto or integrated thereto, at least one male or mound portion or raised padded projection 20. The at least one male or mound portion 20, has at least one central portion 26, and a base or peripheral or pad joining portion 24. The at least one central portion 26, has a height H, a width W, and a length L, (shown in FIG. 5). The at least one male or mound portion 20, has at least one second or mound fluid absorbing material 22. For some applications the at least one male or mound portion 20, and the at least one mound fluid absorbing material 22, could be one and the same thing or interchangeable. The base or peripheral or pad joining portion 24, integrates or joins into the upper or top surface 13, of the base or pad 10. For some applications the base or peripheral or pad joining portion 24, and the upper or top surface 13, of the base or pad 10, could be one and the same thing or interchangeable, as they could be seamlessly integrated or joined to each other. It should be understood that the fluid being absorbed by the at least one mound fluid absorbing material 22, could continue to flow towards the bottom surface 11, of the base or pad 10, and be further absorbed by the base fluid absorbing material 12.

For some applications the inventive sanitary pad with a crevice mound or hygiene device 23, could also have at least one layer of at least one thin plastic backing or material or fluid impervious layer 18, adhered or secured to at least a portion of the base 10, so as to prevent any leakage of bodily fluids or fluid discharge 150, that is being absorbed by the mound fluid absorbing material 22, and the base fluid absorbing material 12, and to further prevent any leakage of bodily fluids or fluid discharge 150, throughout the area, such as, the legs or thighs 130, buttock area 120, vaginal area 123. The at least one thin plastic backing or fluid impervious layer 18, would be between the base or pad 10, and the at least one adhesive 14, thus, for example, the at least one adhesive 14, would be adhered or secured to the bottom or first surface of the thin plastic backing or fluid impervious layer 18, while the pad 10, could be secured to the top or second surface of the thin plastic backing or fluid impervious layer 18.

Figure 2:
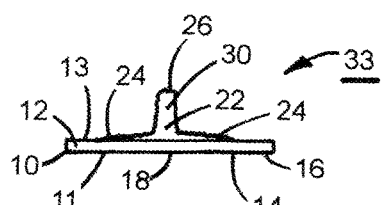
FIG. 2, illustrates a side view of an inventive sanitary pad with a crevice mound, according to a second embodiment of this invention.

FIG. 2, illustrates a side view of an inventive sanitary pad with a crevice mound or hygiene device 33, according to a second embodiment of this invention. The material and the functioning of inventive sanitary pad 33, are same as or similar to the inventive sanitary pad 23, except that the mound or male portion 30, has a narrower width W, from the base or peripheral or pad joining portion 24, to the central portion 26, creating a more narrower male or mound portion 30.

Figure 3:
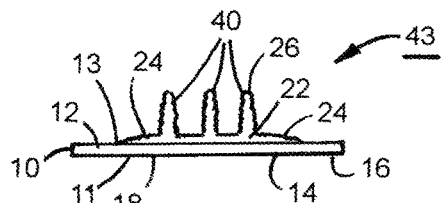
FIG. 3, illustrates a side view of an inventive sanitary pad with a crevice mound, according to a third embodiment of this invention.

FIG. 3, illustrates a side view of an inventive sanitary pad with a crevice mound or hygiene device 43, according to a third embodiment of this invention. The material and the functioning of inventive sanitary pad 43, are same as or similar to the inventive sanitary pad 23, 33, except that the mound or male portion 40, comprises of several mound or male portions 40, and each of the mound or male portion 40, have a narrower width W, from the base or peripheral or pad joining portion 24, to the central portion 26, creating several more narrower male or mound portion 40.

Figure 4:
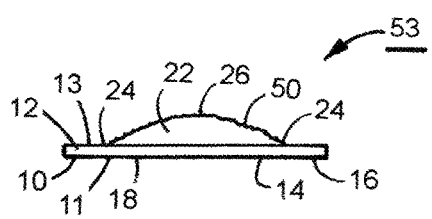
FIG. 4, illustrates a side view of an inventive sanitary pad with a crevice mound, according to a fourth embodiment of this invention.

FIG. 4, illustrates a side view of an inventive sanitary pad with a crevice mound or hygiene device 53, according to a fourth embodiment of this invention. The material and the functioning of inventive sanitary pad 53, are same as or similar to the inventive sanitary pad 23, except that the mound or male portion 50, has a wider width W, from the base or peripheral or pad joining portion 24, to the central portion 26, creating a more wider male or mound portion 50.

Figure 5:
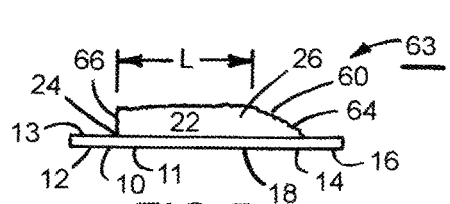
FIG. 5, illustrates a side view of an inventive sanitary pad with a crevice mound, according to a fifth embodiment of this invention.

FIG. 5, illustrates a side view of an inventive sanitary pad with a crevice mound or hygiene device 63, according to a fifth embodiment of this invention. The material and the functioning of inventive sanitary pad 63, are same as or similar to the inventive sanitary pad 23, 33, 43, 53, except that the mound or male portion 60, has an elongated length L, when viewed from the base or peripheral or pad joining portion 24, to the central portion 26, creating a more elongated male or mound portion 60. The elongated male or mound portion 60, has a first or front end 64, that slopes down and gradually integrates with the base or peripheral or pad joining portion 24, and a second or back end 66, that slopes substantially straight down to integrate with the base or peripheral or pad joining portion 24.

Figure 6:
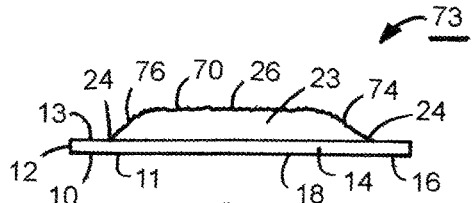
FIG. 6, illustrates a side view of an inventive sanitary pad with a crevice mound, according to a sixth embodiment of this invention.

FIG. 6, illustrates a side view of an inventive sanitary pad with a crevice mound or hygiene device 73, according to a sixth embodiment of this invention. The material and the functioning of inventive sanitary pad 73, are same as or similar to the inventive sanitary pad 23, 33, 43, 53, except that the mound or male portion 70, has an elongated length L, when viewed from the base or peripheral or pad joining portion 24, to the central portion 26, creating a more elongated male or mound portion 70. The elongated male or mound portion 70, has a first or front end 74, which slopes down and gradually integrates with the base or peripheral or pad joining portion 24, and a second or back end 76, that slopes down and gradually integrates with the base or peripheral or pad joining portion 24.

Figure 7:
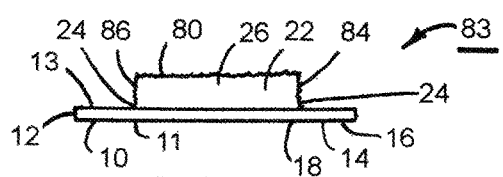
FIG. 7, illustrates a side view of an inventive sanitary pad with a crevice mound, according to a seventh embodiment of this invention.

FIG. 7, illustrates a side view of an inventive sanitary pad with a crevice mound or hygiene device 83, according to a seventh embodiment of this invention. The material and the functioning of inventive sanitary pad 83, are same as or similar to the inventive sanitary pad 23, 33, 43, 53, except that the mound or male portion 80, has an elongated length L, when viewed from the base or peripheral or pad joining portion 24, to the central portion 26, creating a more elongated male or mound portion 80. The elongated male or mound portion 80, has a first or front end 84, that slopes substantially straight down to integrate with the base or peripheral or pad joining portion 24, and a second or back end 86, that slopes substantially straight down to integrate with the base or peripheral or pad joining portion 24.

Figure 8:
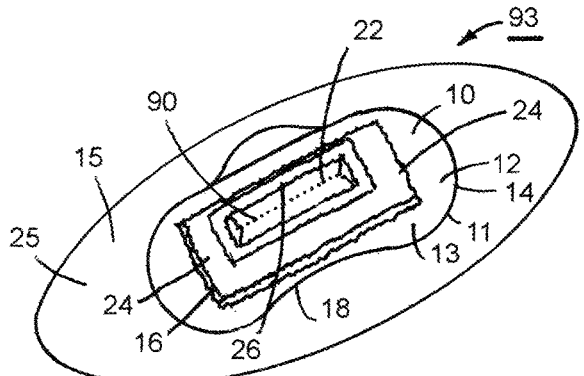
FIG. 8, illustrates a perspective view of an inventive sanitary pad with a crevice mound, according to an eighth embodiment of this invention.

FIG. 8, illustrates a perspective view of an inventive sanitary pad with a crevice mound or hygiene device 93, according to an eighth embodiment of this invention. The material and the functioning of inventive sanitary pad 93, are same as or similar to the inventive sanitary pad 23, 33, 43, 53, 63, 73, 83, except that the mound or male portion 90, is substantially in a shape of an inverted "V" or a prism when viewed along the width "W", and this substantially inverted "V" or prism shape continues along the elongated length L, when viewed from the base or peripheral or pad joining portion 24, to the central portion 26, creating the elongated inverted "V" or prism male or mound portion 90. The protective layer 16, of the inventive sanitary pad 93, has been removed so that the at least one adhesive 14, can be securely and temporarily secured to an inner surface 15, of an underwear 25.

Figure 9:
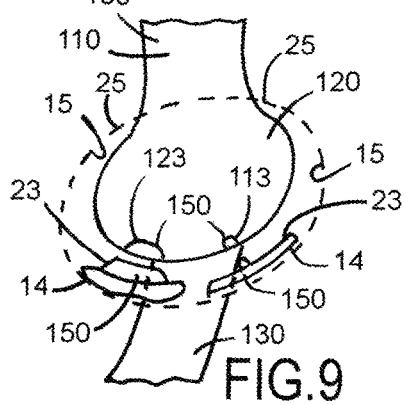
FIG. 9, illustrates a side view of an inventive sanitary pad with a crevice mound as being used by a human.

FIG. 9, illustrates a side view of an inventive sanitary pad with a crevice mound or hygiene device 23, 33, 43, 53, 63, 73, 83, 93, as being used by a human 100. As one can see that the human 100, has a torso area 110, a buttock area 120, and a legs or thigh area 130. The buttock area 120, has an anus or anal area or anal crevice 113, and/or a vagina or vaginal area or vaginal crevice 123. The vagina or vaginal area 123, further comprises of labia majora, labia minora, urethral opening, etc., which are well-known to a person skilled in the art, and for the ease of understanding are not being illustrated here in detail. During use of the inventive sanitary pad 23, 33, 43, 53, 63, 73, 83, 93, one would place the inventive sanitary pad 23, 33, 43, 53, 63, 73, 83, 93, near the point of fluid discharge, such as, the anal area 113, and/or the vaginal area 123, such that at least a portion of the male or mound portion 20, 30, 40, 50, 60, 70, 80, 90, is near and in physical contact with the fluid discharge area, namely, the anal area or anal crevice 113, and/or the vaginal area or vaginal crevice 123. It should be understood that the shape of the mound or male portion 20, 30, 40, 50, 60, 70, 80, 90, is such that at least a portion of the mound or male portion 20, 30, 40, 50, 60, 70, 80, 90, penetrates the vagina or vaginal area or vaginal crevice 123, and could be held in place, for example, by at least a portion of labia majora or at least a portion between the left labia majora and the right labia majora. Thus, any fluid discharge 150, from the vaginal area 123, would first flow near or around the labia minora area 123, and then near or around the labia majora area 123, and would be intercepted as close as possible at the point of fluid discharge by the inventive mound or male portion 20, 30, 40, 50, 60, 70, 80, 90, of the inventive sanitary pad 23, 33, 43, 53, 63, 73, 83, 93. Similarly, when there is any fluid discharge 150, from the anal area 113, because the inventive mound or male portion 20, 30, 40, 50, 60, 70, 80, 90, is wedged in and around the anus or anal area 113, it would be intercepted as close as possible at the point of fluid discharge by the inventive mound or male portion 20, 30, 40, 50, 60, 70, 80, 90, of the inventive sanitary pad 23, 33, 43, 53, 63, 73, 83, 93. Thus, when there is a discharge of a human fluid 150, either from the anal area 113, and/or the vaginal area 123, the male or mound portion 20, 30, 40, 50, 60, 70, 80, 90, of the inventive sanitary pad 23, 33, 43, 53, 63, 73, 83, 93, would immediately intercept and absorb the human discharged fluid 150, via the at least one second fluid absorbing material 22, and any excess or extra human discharged fluid 150, would be absorbed by the at least one first fluid absorbing material 12, thus leaving the human 100, dry of any discharged bodily or human fluid 150. It is preferred that the human 100, place the inventive sanitary pad 23, 33, 43, 53, 63, 73, 83, 93, near the point of fluid discharge, such as, the anal area or anal crevice 113, and/or the vaginal area or vaginal crevice 123, first, and then remove the protective layer 16, from the bottom surface 11, before wearing or putting-on the underwear 25. This way, the human 100, is sure that the inventive sanitary pad 23, 33, 43, 53, 63, 73, 83, 93, is correctly placed at or near the point of fluid discharge, such as, the anal area 113, and/or the vaginal area 123, and the adhesive 14, would prevent any sliding of the inventive sanitary pad 23, 33, 43, 53, 63, 73, 83, 93, during use, as it would be securely and temporarily being attached to the inside surface 15, of the underwear 25.

Figure 10:
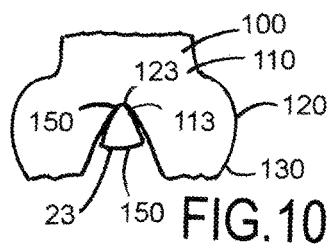
FIG. 10, illustrates a front view of an inventive sanitary pad with a crevice mound as being used by a human.

FIG. 10, illustrates a front view of an inventive sanitary pad with a crevice mound 23, 33, 43, 53, 63, 73, 83, 93, as being used by a human 100. As one can see that the inventive sanitary pad with a crevice mound 23, 33, 43, 53, 63, 73, 83, 93, flush mounts to the vaginal area 123, and or anal area 113, and intercepts the discharged fluid 150, as it is leaving the human 100, almost at or near the point of discharge or source. The fluid absorbing material 12, 22, is flexible and body conforming, and thus the inventive sanitary pad with a crevice mound 23, 33, 43, 53, 63, 73, 83, 93, almost follows the contours of the anal area 113, or vaginal area 123, when the inventive sanitary pad with a crevice mound 23, 33, 43, 53, 63, 73, 83, 93, is placed in use or in situ.

It should be appreciated that the mound or male portion 20, 30, 40, 50, 60, 70, 80, 90, of the inventive sanitary pad with a crevice mound or hygiene device 23, 33, 43, 53, 63, 73, 83, 93, does not penetrate the vagina 123, like a tampon, but hugs or cresses the labia majora 123, and/or labia minora 123, so in a sense it conforms to the cavity or crevice formed by the labia majora 123, i.e., the left labia majora 123, and the right labia majora 123.

It should be understood that the discharge of a human fluid 150, from the anal area 113, could be due to, for example, anal bleeding 150, fecal incontinence 150, loose bowl movement 150, gaseous discharge with particulates 150, to name a few, while the discharge of the human fluid 150, from the vaginal area 123, could be due to, for example, urinary incontinence 150, menstrual flow or menses 150, discharge due to vaginal diseases 150, to name a few.

It should be appreciated that the mound or male portion 20, 30, 40, 50, 60, 70, 80, 90, would first intercept the human fluid discharge 150, and the captured human fluid discharge 150, would be initially retained by the second fluid absorbing material 22, while any excess human fluid discharge 150, would be captured and retained by the first fluid absorbing material or pad 10, thus leaving the human 100, dry of any discharged bodily or human fluid 150.

It should be understood that the first fluid absorbing material 12, or pad 10, is made of a material that can capture and retain fluids or liquids 150, and that the first fluid absorbing material 12, or pad 10, is physically connected to the second fluid absorbing material 22, or pad 20, and that the second fluid absorbing material 22, or pad 20, is also made of a material that can capture and retain fluids or liquids 150. Thus, and captured fluid or liquid 150, captured by either pad 10, or pad 20, could move or migrate from pad 10, to pad 20, and vice versa.

The shape of the mound or male portion 20, 30, 40, 50, 60, 70, 80, 90, of the inventive sanitary pad with a crevice mound or hygiene device 23, 33, 43, 53, 63, 73, 83, 93, can be selected from a group comprising a wall, a pyramid, a mound, a hill, a wedge, a prism, a wall having sloping edges, a wall having sharp right-angled edges, a raised central portion with peripheral sloping portion, and combinations thereof, to name a few.

The cross-sectional shape of the mound or male portion 20, 30, 40, 50, 60, 70, 80, 90, of the inventive sanitary pad with a crevice mound or hygiene device 23, 33, 43, 53, 63, 73, 83, 93, can be selected from a group comprising a triangle, a square, a rectangle, a circle, an oval, a polygonal shape, a cylindrical shape, and combinations thereof, to name a few.

The height "H" for the inventive sanitary pad with a crevice mound or hygiene device 23, 33, 43, 53, 63, 73, 83, 93, can be selected from a group comprising ¼ inch, ½ inch, ¾ inch, 1 inch, 1 and ¼ inch, 1 and ½ inch, 1 and ¾ inch, 2 inches, and combination thereof, to name a few.

However, for some applications the height "H" for the inventive sanitary pad with a crevice mound or hygiene device 23, 33, 43, 53, 63, 73, 83, 93, can be selected from a group comprising between about ¼ inch to about 2 inches, and preferably between about ½ inch to about 1 and ½ inches, and more preferably about ¾ inches to about 1 and ¼ inches, and combination thereof, to name a few.

The width "W" for the inventive sanitary pad with a crevice mound or hygiene device 23, 33, 43, 53, 63, 73, 83, 93, can be selected from a group comprising ¼ inch, ½ inch, ¾ inch, 1 inch, 1 and ¼ inch, 1 and ½ inch, 1 and ¾ inch, 2 inches, and combination thereof, to name a few.

However, for some applications the width "W" for the inventive sanitary pad with a crevice mound or hygiene device 23, 33, 43, 53, 63, 73, 83, 93, can be selected from a group comprising between about ¼ inch to about 2 inches, and preferably between about ½ inch to about 1 and ½ inches, and more preferably about ¾ inches to about 1 and ¼ inches, and combination thereof, to name a few.

The length "L" for the inventive sanitary pad with a crevice mound or hygiene device 23, 33, 43, 53, 63, 73, 83, 93, can be selected from a group comprising between about 1 inch to about 6 inches, and preferably between about 2 inches to about 5 inches, and more preferably about 3 inches to about 4 inches, and combination thereof, to name a few.

Thus, the present invention is not limited to the embodiments described herein and the constituent elements of the invention can be modified in various manners without departing from the spirit and scope of the invention. Various aspects of the invention can also be extracted from any appropriate combination of a plurality of constituent elements disclosed in the embodiments. Some constituent elements may be deleted in all of the constituent elements disclosed in the embodiments. The constituent elements described in different embodiments may be combined arbitrarily.

Still further, while certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions.

It should be further understood that throughout the specification and claims several terms have been used and they take the meanings explicitly associated herein, unless the context clearly dictates otherwise. For example, the phrase "in one embodiment" as used herein does not necessarily refer to the same embodiment, though it may. Additionally, the phrase "in another embodiment" as used herein does not necessarily refer to a different embodiment, although it may. Thus, various embodiments of the invention may be readily combined, without departing from the scope or spirit of the invention.

While the present invention has been particularly described in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A hygiene device, comprising:
   (a) at least one first fluid absorbing layer having a top surface and a bottom surface;
   (b) at least one second fluid absorbing layer, wherein said second fluid absorbing layer is in physical contact with said top surface of said at least one first fluid absorbing layer, and wherein said at least one second fluid absorbing layer comprises of a plurality of male portions;
   (c) at least one layer of at least one fluid impervious material secured to at least a portion of said bottom surface of said at least one first fluid absorbing layer; and
   (d) wherein at least a portion of said plurality of male portions is configured to penetrate vaginal crevice.

2. The hygiene device of claim 1, wherein at least one male portion from said plurality of male portions has a height H, a length L, and a width W, and wherein said height H is between about ¼ inch to about 2 inches, and wherein said length L is between about 1 inch to about 6 inches, and said width W is between about ¼ inch to about 2 inches.

3. The hygiene device of claim 1, wherein shape of at least one male portion from said plurality of male portions is selected from a group consisting of a wall, a pyramid, a mound, a hill, a wedge, a prism, a wall having sloping edges, a wall having sharp right-angled edges, a raised central portion with peripheral sloping portion, and combinations thereof.

4. The hygiene device of claim 1, wherein at least one male portion from said plurality of male portions of said at least one second fluid absorbing layer is disposed to be placed inside an anal area.

5. The hygiene device of claim 1, wherein at least one male portion from said plurality of male portions of said at least one second fluid absorbing layer is disposed to be placed one of adjacent labia minora, and inside an anal area.

6. The hygiene device of claim 1, wherein at least one male portion from said plurality of male portions of said at least one second fluid absorbing layer is disposed to be placed adjacent labia majora.

7. The hygiene device of claim 1, wherein at least one male portion from said plurality of male portions of said at least one second fluid absorbing layer is disposed to be placed adjacent labia majora such that at least a portion of said at least one male portion of said at least one second fluid absorbing layer is adjacent at least a portion of labia majora.

8. The hygiene device of claim 1, wherein at least one male portion from said plurality of male portions of said at least one second fluid absorbing layer is disposed to be placed adjacent labia minora.

9. A hygiene device, comprising:
(a) at least one first fluid absorbing layer having a top surface and a bottom surface;
(b) at least one second fluid absorbing layer, wherein said second fluid absorbing layer is in physical contact with said top surface of said at least one first fluid absorbing layer, and wherein said at least one second fluid absorbing layer comprises of a plurality of male portions;
(c) at least one layer of at least one fluid impervious material secured to at least a portion of said bottom surface of said at least one first fluid absorbing layer; and
(d) wherein at least a portion of said plurality of male portions is configured to penetrate vaginal crevice.

10. The hygiene device of claim 9, wherein at least one layer of at least one adhesive is secured to at least a portion of said at least one layer of at least one fluid impervious material.

11. The hygiene device of claim 10, wherein at least one layer of at least one thin plastic backing is secured to at least a portion of said at least one layer of said at least one adhesive.

12. The hygiene device of claim 9, wherein shape of at least one male portion from said plurality of male portions is selected from a group consisting of a wall, a pyramid, a mound, a hill, a wedge, a prism, a wall having sloping edges, a wall having sharp right-angled edges, a raised central portion with peripheral sloping portion, and combinations thereof.

13. The hygiene device of claim 9, wherein at least one male portion from said plurality of male portions of said at least one second fluid absorbing layer is disposed to be placed inside an anal area.

14. A hygiene device in the nature of a pad, comprising:
(a) at least one first fluid absorbing layer having a top surface and a bottom surface;
(b) at least one second fluid absorbing layer, wherein said second fluid absorbing layer is in physical contact with said top surface of said at least one first fluid absorbing layer, and wherein said at least one second fluid absorbing layer comprises of a plurality of male portions;
(c) at least one layer of at least one fluid impervious material secured to at least a portion of said bottom surface of said at least one first fluid absorbing layer; and
(d) wherein at least one male portion from said plurality of male portions is disposed to be placed inside a user's vaginal crevice.

15. The hygiene device in the nature of a pad of claim 14 wherein at least one male portion from said plurality of male portions has a height H, a length L, and a width W, and wherein said height H is between about ¼ inch to about 2 inches, and wherein said length L is between about 1 inch to about 6 inches, and said width W is between about ¼ inch to about 2 inches.

16. The hygiene device in the nature of a pad of claim 14, wherein at least one layer of at least one adhesive is secured to at least a portion of said at least one layer of at least one fluid impervious material.

17. The hygiene device in the nature of a pad of claim 14, wherein shape of at least one male portion from said plurality of male portions is selected from a group consisting of a wall, a pyramid, a mound, a hill, a wedge, a prism, a wall having sloping edges, a wall having sharp right-angled edges, a raised central portion with peripheral sloping portion, and combinations thereof.

18. The hygiene device in the nature of a pad of claim 14, wherein at least one male portion from said plurality of male portions of said at least one second fluid absorbing layer is disposed to be placed adjacent labia majora.

19. The hygiene device in the nature of a pad of claim 14, wherein at least one male portion from said plurality of male portions of said at least one second fluid absorbing layer is disposed to be placed adjacent labia majora such that at least a portion of said at least one male portion of said at least one second fluid absorbing layer is adjacent at least a portion of labia majora.

20. The hygiene device in the nature of a pad of claim 14, wherein at least one male portion from said plurality of male portions of said at least one second fluid absorbing layer is disposed to be placed one of adjacent labia minora, and inside an anal area.

* * * * *